United States Patent
Yago et al.

(10) Patent No.: US 8,734,695 B2
(45) Date of Patent: May 27, 2014

(54) ENDOSCOPE FLEXIBLE TUBE AND ITS MANUFACTURING METHOD

(75) Inventors: Atsushi Yago, Saitama (JP); Nobuharu Takahashi, Saitama (JP); Yoshiyuki Yoshimoto, Saitama (JP); Rei Miyasaka, Shizuoka (JP)

(73) Assignee: Fujinon Corporation, Saitama-shi (JP)

( * ) Notice: Subject to any disclaimer, the term of this patent is extended or adjusted under 35 U.S.C. 154(b) by 1127 days.

(21) Appl. No.: 12/200,564

(22) Filed: Aug. 28, 2008

(65) Prior Publication Data

US 2009/0112066 A1  Apr. 30, 2009

(30) Foreign Application Priority Data

Oct. 25, 2007 (JP) ............... P2007-277891
Oct. 25, 2007 (JP) ............... P2007-277892
Oct. 31, 2007 (JP) ............... P2007-283588
Oct. 31, 2007 (JP) ............... P2007-283589

(51) Int. Cl.
*B32B 1/00* (2006.01)

(52) U.S. Cl.
USPC .............. 264/171.13; 264/171.1; 264/171.11; 264/171.12; 264/171.17; 264/171.26; 264/171.27; 264/241; 264/251; 264/254; 264/255; 264/260; 264/262; 264/263; 264/271.1; 264/563; 264/555; 264/512; 264/513; 264/514; 264/515; 264/444; 264/445; 264/510; 264/149

(58) Field of Classification Search
USPC .............. 264/171.1–171.13, 510, 563, 176.1, 264/177.14, 171.17, 171.26, 171.27, 241, 264/251, 254, 255, 260, 262, 263, 271.1, 264/555, 512–515, 444, 445, 149
See application file for complete search history.

(56) References Cited

U.S. PATENT DOCUMENTS

| | | | |
|---|---|---|---|
| 4,250,072 A | 2/1981 | Flynn | |
| 5,614,136 A | 3/1997 | Pepin et al. | |
| 5,622,665 A | 4/1997 | Wang | |
| 6,458,075 B1 | 10/2002 | Sugiyama et al. | |
| 2002/0010386 A1 | 1/2002 | Matsushita et al. | |
| 2004/0193013 A1 | 9/2004 | Iwasaka et al. | |

FOREIGN PATENT DOCUMENTS

| | | |
|---|---|---|
| DE | 10020653 A1 | 11/2000 |
| JP | 55-112505-UM | 8/1980 |
| JP | 2-131738 A | 5/1990 |
| JP | 5-23398 A | 2/1993 |
| JP | 5-25156 U | 4/1993 |
| JP | 8-24212 A | 1/1996 |

(Continued)

OTHER PUBLICATIONS

Chinese Office Action (with English translation) issued Feb. 12, 2010 for corresponding Chinese Application No. 200810214944.3.

(Continued)

*Primary Examiner* — Jeffrey Wollschlager
*Assistant Examiner* — Stella Yi
(74) *Attorney, Agent, or Firm* — Birch, Stewart, Kolasch & Birch, LLP

(57) ABSTRACT

An endoscope flexible tube comprises: a tubular structure having flexibility; and a shell layer on an outer peripheral surface of the tubular structure, wherein the shell layer has a two-layer structure including a rigid resin layer of a rigid resin and a soft resin layer of a soft resin, and wherein the two-layer structure is maintained over the entire flexible tube in its length direction.

6 Claims, 14 Drawing Sheets

(56) References Cited

FOREIGN PATENT DOCUMENTS

| | | | |
|---|---|---|---|
| JP | 8-57035 A | | 3/1996 |
| JP | 8-304712 A | | 11/1996 |
| JP | 08304712 | * | 11/1996 |
| JP | 2001-56076 A | | 2/2001 |
| JP | 2001-70450 A | | 3/2001 |
| JP | 2001-321324 A | | 11/2001 |
| JP | 2003-113965 A | | 4/2003 |
| JP | 3586928 B2 | | 8/2004 |
| JP | 2006-109997 A | | 4/2006 |
| JP | 2007-159775 A | | 6/2007 |
| WO | WO-96/26825 A1 | | 9/1996 |
| WO | WO-99/61091 A2 | | 12/1999 |

OTHER PUBLICATIONS

Japanese Notification of Reasons for Refusal dated Oct. 14, 2011 for Japanese Application No. 2007-283588.

Japanese Office Action (with English translation) issued on Nov. 11, 2011 for Japanese Application No. 2007-283589.

Japanese Office Action dated Sep. 21, 2012 for Application No. 2007-283589.

\* cited by examiner

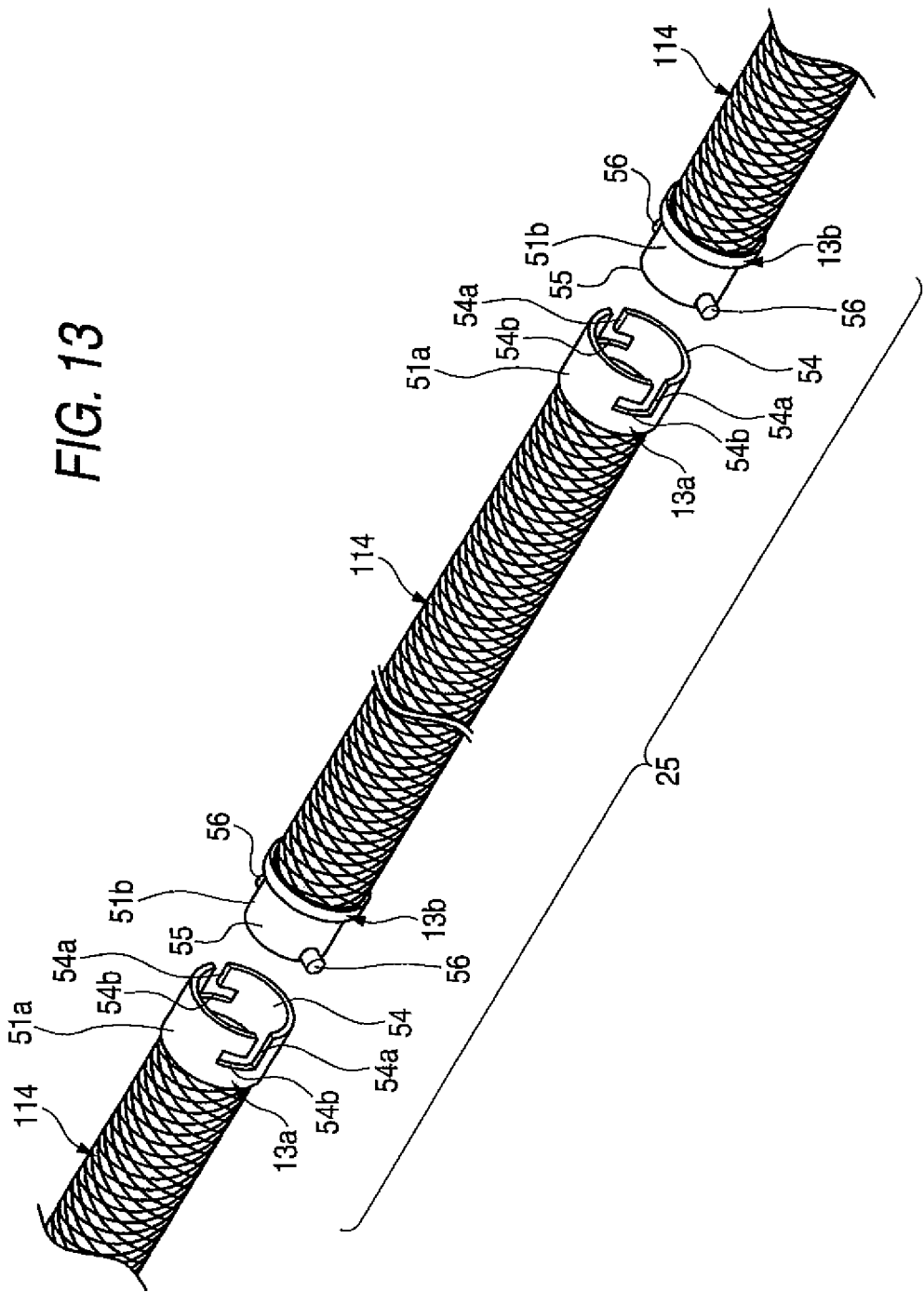

ENDOSCOPE FLEXIBLE TUBE AND ITS MANUFACTURING METHOD

BACKGROUND OF THE INVENTION

1. Field of the Invention

The present invention relates to an endoscope flexible tube and its manufacturing method for manufacturing a flexible tube constituting an insertion portion of an endoscope.

2. Description of the Related Art

Endoscopes for medical treatment for observing the insides of patient's body cavities are known. These endoscopes include an insertion portion to be inserted into patient's body cavities, and an operation portion provided at a distal end of the insertion portion. Inside the insertion portion, a treatment tool insertion tube, a light guide which transmits illumination light, a signal cable, and a bending wire which bends the insertion portion, etc. are provided from the distal side to the proximal side.

It is general that the flexible tube which is a main part which constitutes the insertion portion of the endoscope is composed of a spiral tube formed by winding a metallic strip spirally, a tubular net body which covers this helical tube, and a shell layer made of a urethane resin, etc. which is laminated on the surface of the tubular net body. In this case, it is preferable that the pliability at the distal side be high in order to make the insertion portion easily inserted into body cavities, and the pliability at the proximal side of the aforementioned flexible tube be low in order to facilitate operation. Thus, when the flexible tube is manufactured, as described in JP-UM-55-112505, it is suggested that two kinds of rigid and soft resins are used to form a shell layer having a two-layer structure of a soft resin layer and a rigid resin layer such that the ratio of the soft resin is high at the distal side, and the ratio of the rigid resin is soft at the proximal side. Further, in an endoscope flexible tube described in JP-A-2007-159775, a shell layer is constituted by only a soft resin layer at the distal side of the endoscope flexible tube, and the shell layer is constituted by only a rigid resin layer on the proximal side thereof.

Further, in order to efficiently the step of molding the shell layer of such a flexible tube, the configuration of an endoscope flexible tube and a manufacturing method which continuously performs molding of the shell layer while a plurality of flexible tubes are conveyed in a state where they are connected integrally is described in Japanese Patent No. 3586928.

In a case where the shell layer of the flexible tube as described in JP-UM-A-55-112505, and JP-A-2007-159775 is continuously molded as described in Japanese Paten No. 3586928, the molding is performed while the soft resin and the rigid resin are supplied to molding dies, respectively, by an extruder. Therefore, in order to constitute the outer shell with only either the soft resin or the rigid resin layer and set the thickness of the other thereof to zero, it is necessary to stop discharge of the resins by the extruder or to provide bypass passages which makes resins flow out of the molding dies.

However, it is very difficult to adjust the discharge amounts of the resins to the molding dies to zero, and since there are portions (welds) in which the resins stagnate inside the molding dies even if the discharge amounts are set to zero, it is difficult to set the thicknesses of the resins to zero. Moreover, in a case where the discharge amounts are increased gradually after the discharge amounts are set to zero, the resins which have stagnated inside the molding dies are extruded and molded. Therefore, the molding thicknesses of the resins in the circumferential direction of the flexible tube do not become uniform, but nonuniformity will be caused.

SUMMARY OF THE INVENTION

The present invention has been made in consideration of the above situations. It is therefore an object of the invention to provide an endoscope flexible tube in which a soft resin layer and a rigid resin layer of the flexible tube are molded such that their thicknesses in the peripheral direction are uniform, and their molding thicknesses in the axial direction are adjusted precisely.

Further, a configuration in which a soft resin and a rigid resin are mixed and molded, and flexibility is changed by the mixing ratio of the resins is described in JP-A-2-131738.

In a case where the shell layer of the flexible tube as described in JP-UM-A-55-112505, and JP-A-2-131738 is molded by the manufacturing method described in Japanese Paten No. 3586928, the molding of the shell layer is continuously performed while a plurality of helical tubes which are connected together via a connecting member and are covered with a tubular net body. Therefore, when the shell layer is molded in portions of the helical tubes, the shell layer is molded such that the rigid resin increases gradually and the soft resin decreases gradually, toward the proximal side from the distal side, and thereafter, the ratio of the rigid resin and the soft resin should be returned to an initial value to the position of the distal end of the next helical tube. Consequently, the ratio should be reversed such that the rigid resin decreases and the soft resin increases, at the portion of the connecting member. However, in Japanese Patent No. 3586928, the molding is performed while the resins to be molded are always to the molding dies. Therefore, it is difficult to steeply change the ratio of the soft resin and the rigid resin while the molding is performed in the position of the connecting member. Thus, although it is conceivable that the ratio of the rigid resin and the soft resin is returned to an initial value by making the length of the connecting member almost the same length as the helical tube to thereby sufficiently secure the conveyance time from the position of the proximal end of the helical tube to the position of the distal end of the next helical tube. However, as the connecting member become longer, the number of flexible tubes which can be molded at a time in a molding step decreases further, and the resin of such amount that the shell layer of the connecting member is molded becomes unnecessary. Therefore, the manufacturing efficiency is bad, which causes an increase in cost.

The present invention has been made in consideration of the above situations. It is therefore an object of the invention to provide a manufacturing method of an endoscope flexible tube capable of efficiently molding an outer layer of a flexible tube, and capable of being manufactured at low cost.

Further, in the molding step of a shell layer as described above, in order to connect a plurality of flexible tubes integrally, as described in, for example, JP-A-2001-70450, connecting rings are formed by screwing both ends of a tubular net body which covers a helical tube, and C-shaped clips are hooked and connected to the connecting rings.

However, in the manufacturing method like JP-A-2001-70450, flexible tubes are connected by using connecting jigs, such as C-shaped clips, or forming connecting rings which are not needed in the state of products. Therefore, the job of forming the connecting rings or attaching the jigs is troublesome. Further, the jigs are prepared as many as the flexible tube are connected, which causes an increase in manufacturing cost. Further, if the C-shaped clips are not put into a state where a tension is applied thereto in the longitudinal direction, there is a problem in that the clips are readily disengaged from the connecting rings.

The present invention has been made in consideration of the above situations. It is therefore an object of the invention to provide a manufacturing method of an endoscope flexible tube capable of performing molding of a shell layer without using any jigs, and with a coupled state held.

The invention is as follows.

(1) An endoscope flexible tube comprises: a tubular structure having flexibility; and a shell layer on an outer peripheral surface of the tubular structure, wherein the shell layer has a two-layer structure including a rigid resin layer of a rigid resin and a soft resin layer of a soft resin, and wherein the two-layer structure is maintained over the entire flexible tube in its length direction.

(2) The endoscope flexible tube according to the above (1), wherein a thickness ratio of the soft resin layer and the rigid resin layer falls within a range of 1:9 to 9:1.

(3) The endoscope flexible tube according to the above (1) or (2), wherein the shell layer is molded such that a thickness ratio of the soft resin layer is larger than that of the rigid resin layer at one end of the flexible tube, a thickness of the rigid resin layer increases gradually toward the other end from the one end, and the thickness ratio of the rigid resin layer is larger than that of the soft resin layer at the other end of the flexible tube.

(4) The endoscope flexible tube according to any one of the above (1) to (3), wherein the shell layer has a uniform external diameter over the entire flexible tube.

(5) The endoscope flexible tube according to any one of the above (1) to (4), wherein the tubular structure comprises: a spiral tube obtained by forming a beltlike piece spirally; and a tubular net body that covers an outer peripheral surface of the spiral tube.

(6) A manufacturing method of an endoscope flexible tube according to any one of the above (1) to (5), the method comprising continuously molding the shell layer including the rigid resin and the soft resin on outer surfaces of a plurality of tubular structures having flexibility while the tubular structures are conveyed in a connected state.

(7) The manufacturing method of an endoscope flexible tube according to the above (6) wherein each of said plurality of tubular structures having flexibility comprises a first coupling portion at its rear end and a second coupling portion at its distal end, and wherein said plurality of tubular structures are connected while the first coupling portion of one of the tubular structures is connected to the second coupling portion of next one of the tubular structures.

(8) The manufacturing method of an endoscope flexible tube according to the above (6), wherein said plurality of tubular structures having flexibility are connected by a connecting member.

(9) The manufacturing method of an endoscope flexible tube according to the above (8), wherein when the shell layer is molded at an outer periphery of the tubular structures, the shell layer is molded such that a ratio of the soft resin is larger than that of the rigid resin at one end of one of the tubular structures, a ratio of the rigid resin increases gradually toward the other end from the one end of the one of the tubular structures, and the ratio of the rigid resin is larger than that of the soft resin at the other end; when the shell layer is molded on an outer periphery of the connecting member, the shell layer is molded such that the ratio of the rigid resin becomes larger than that of the soft resin in a position adjacent to the other end of the one of the tubular structures, the ratio of the soft resin increases gradually from the other end of the one of the tubular structures toward one end of next one of the tubular structures, and the ratio of the soft resin becomes larger than that of the rigid resin in a position adjacent to the one end of the next one of the tubular structures; and a conveyance speed of said plurality of tubular structures when the shell layer is molded at the outer periphery of the connecting member is made slower than that when the shell layer is molded at the outer periphery of the tubular structure.

(10) The manufacturing method of an endoscope flexible tube according to the above (8) or (9), wherein when the shell layer is molded, the shell layer is molded as a two-layer structure in which the rigid resin is formed in a lower layer and the soft resin is formed in an upper layer.

(11) The manufacturing method of an endoscope flexible tube according to the above (8) or (9), wherein at least a portion of the connecting member has a diameter smaller than that of the tubular structures.

(12) The manufacturing method of an endoscope flexible tube according to any one of the above (6) to (8), wherein when the shell layer is molded at an outer periphery of the tubular structures, the shell layer is molded such that a ratio of the soft resin and the rigid resin changes gradually from one end of one of the tubular structures toward the other end of the one of the tubular structures, and then, when the shell layer is molded at an outer periphery of next one of the tubular structure, the shell layer is molded such that the ratio of the soft resin and the rigid resin returns to an initial value at the one end of the one of the tubular structures from one end of the next one of the tubular structures toward the other end of the next one of the tubular structures.

(13) The manufacturing method of an endoscope flexible tube according to the above (12), wherein when the shell layer is molded, the shell layer is molded as a two-layer structure in which the rigid resin is formed in a lower layer, and the soft resin is formed in an upper layer.

Further, the following aspects are also preferable.

(14) The manufacturing method of an endoscope flexible tube according to the above (7) in which the first coupling portion is a female thread portion, and the second coupling portion is a male thread portion screwed to the female thread portion.

(15) The manufacturing method of an endoscope flexible tube in which the first coupling portion is a first cylindrical portion formed with longitudinal slits cut away along the axial direction from an end surface, and lateral slits which are cut away in the peripheral direction continuously with the longitudinal slits, respectively, the second coupling portion is composed of a second cylindrical portion whose outer peripheral surface fits onto the inner peripheral surface of the first cylindrical portion, and convex portions which protrude from the outer peripheral surface of the second cylindrical portion, and if the convex portions are pushed into the longitudinal slits until the convex portions bump against the inner portions of the longitudinal slits by making the second coupling portion fit to the first cylindrical portion while the convex portions are inserted into the longitudinal slits, respectively, and thereafter, the second coupling portion is rotated relative to the first coupling portion, the convex portions are engaged with the lateral slits, respectively, and thereby, the first coupling portion and the second coupling portion are coupled together.

BRIEF DESCRIPTION OF THE DRAWINGS

FIG. 13 is a perspective view showing coupling portions with a configuration separate from coupling portions shown in FIG. 12.

DETAILED DESCRIPTION OF THE INVENTION

Figure 1:
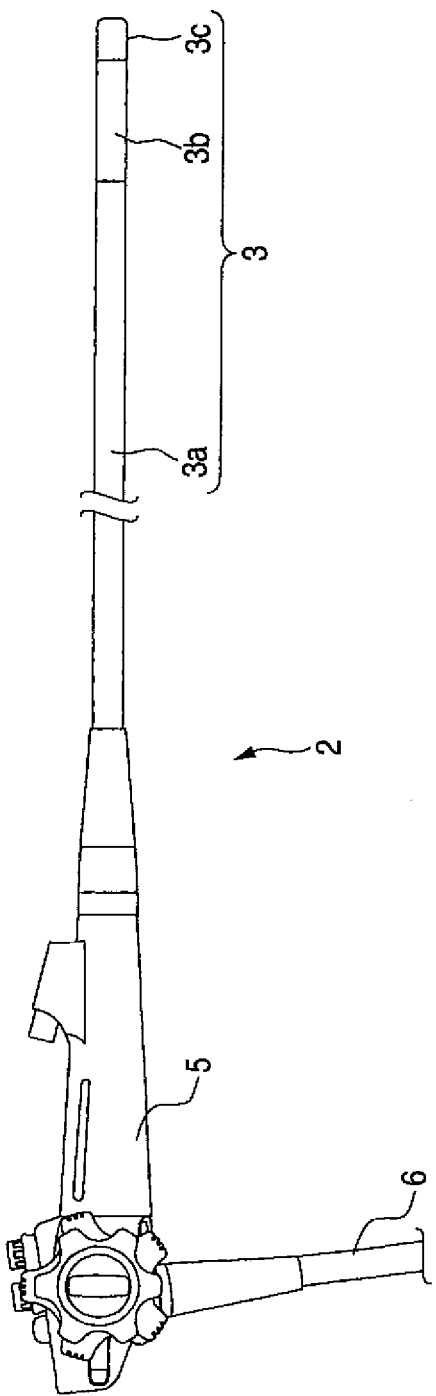
FIG. 1 is a schematic diagram showing the configuration of an endoscope in respective embodiments.

FIG. 1 shows an electronic endoscope into which a flexible tube according to the invention is incorporated. As shown in FIG. 1, the electronic endoscope 2 widely used for medical treatment includes an insertion portion 3 inserted into body cavities, a body operation portion 5 continuously provided at a proximal end of the insertion portion 3, and a universal cord 6 connected to a processor or a light source (not shown) which is an external device. The insertion portion 3 is composed of a flexible tube portion 3a which occupies most of a length from a joining portion to the body operation portion 5, an angle portion 3b continuously provided at the flexible tube portion 3a, and a distal end 3c which is continuously provided at the distal end of the angle portion and has an imaging device for photographing the insides of body cavities (not shown) built therein. The flexible tube portion 3a which occupies most of the length of the insertion portion 3 of the electronic endoscope 2 has flexibility over almost the entire length thereof, and particularly its part to be inserted into cavities has structure with higher flexibility. Hereinafter, respective embodiments about the flexible tube portion will be described.

First Embodiment

Figure 2:
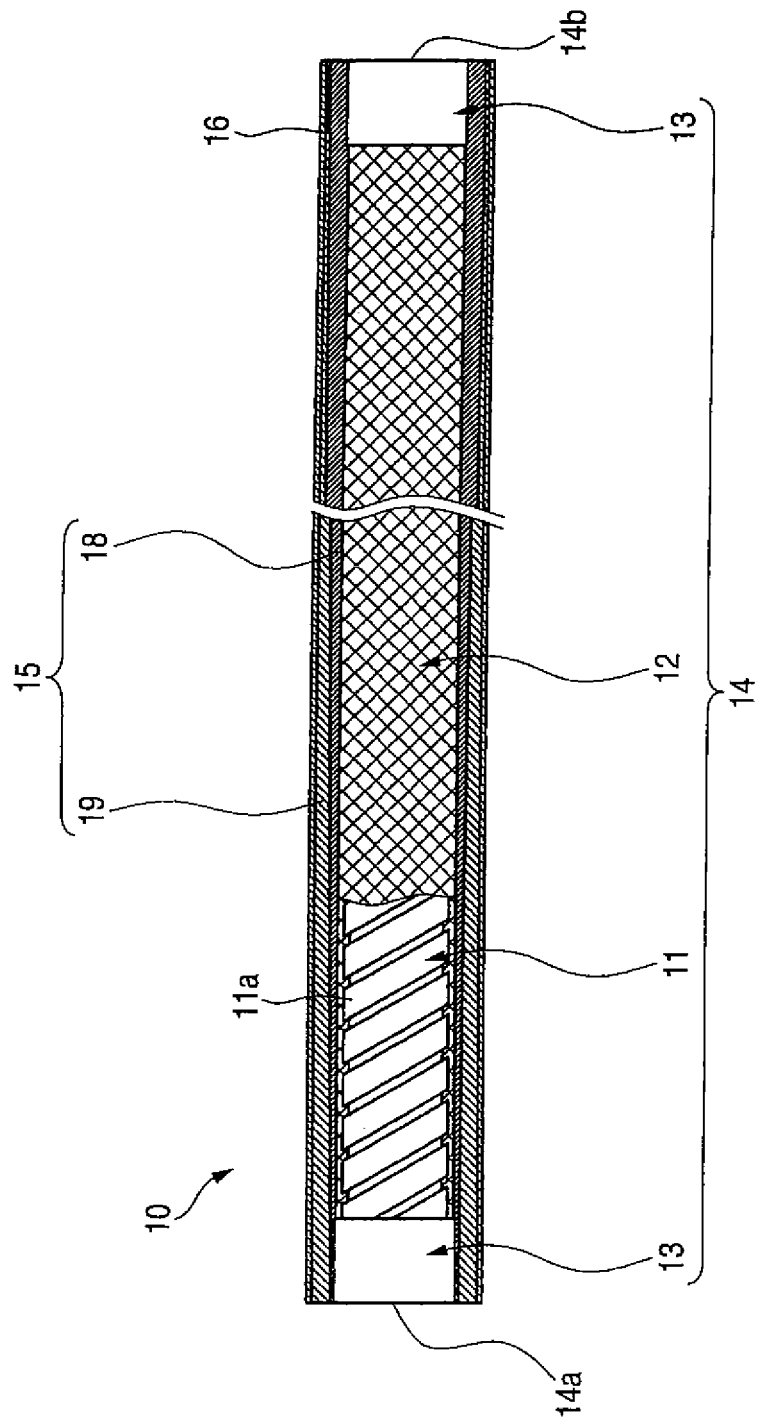
FIG. 2 is an enlarged fragmentary sectional view showing the configuration of an endoscope flexible tube, in a first embodiment.

Specifically, a flexible tube 10 which constitutes the flexible tube portion 3a, as shown in FIG. 2, is configured such that a flexible tube assembly 14 is obtained by covering a helical tube 11 formed by spirally winding a metallic strip 11a on the innermost side with a tubular net body 12 made by weaving a metallic wire, and fitting mouthpieces 13 into both ends thereof, and a shell layer 15 made of urethane resin, etc. is laminated on an outer peripheral surface of the assembly. Further, a coating film 16 which contains, for example, chemical-resistant fluorine, silicone, etc. is coated on an outer surface of the shell layer 15. In addition, the distal end and proximal end of the flexible tube assembly 14 will be described below using reference numerals 14a and 14b, respectively. In this case, the distal end 14a is an end on the side where the aforementioned angle portion 3b is connected, and the proximal end 14b is an end on the side where the body operation portion 5 is connected.

Specifically, as shown in FIG. 2, the shell layer 15 is composed of a soft resin layer 19 and a rigid resin layer 18. The rigid resin layer 18 which is molded at the lower layer is thinly molded at the distal end 14a of the flexible tube assembly 14, and is molded so as to become thick gradually toward the proximal end 14b from the distal end 14a. On the other hand, the soft resin layer 19 which is molded at the upper layer of the rigid resin layer 18 is molded so as to be thickest at the distal end 14a and to become thin gradually toward the rear end from the distal end 14a, and is molded such that the external diameter of the shell layer 15 may become uniform. Thereby, since the flexible tube 10 is structured to have high pliability at the distal end 14a and low pliability at the proximal end 14b, it is possible to give flexibility required for the insertion portion 3 constituted by the flexible tube 10.

Figure 3:
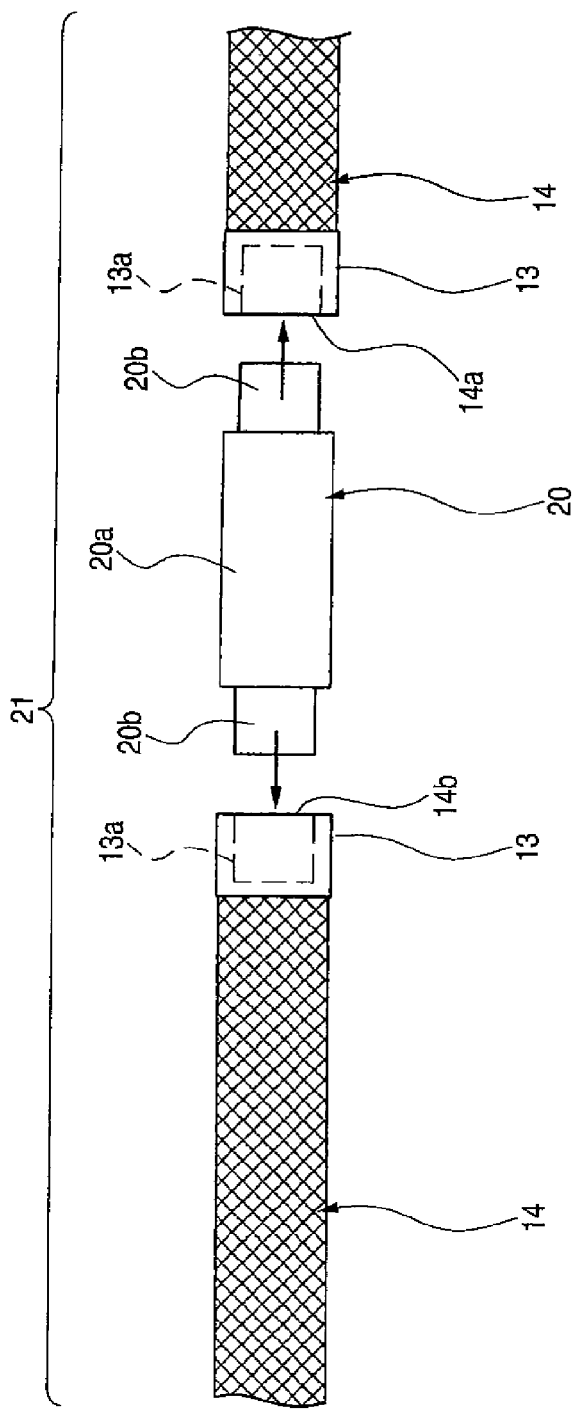
FIG. 3 is a plan view showing the configuration of a joint member which connects flexible tube assemblies together, in the first embodiment.

FIG. 3 shows a state where a joint member 20 and the flexible tube assembly 14 are connected before the shell layer 15 is molded. The joint member 20 includes a main body 20a, and connecting portions 20b inserted into inner peripheral surfaces 13a, respectively, of the mouthpieces 13 on both sides of the main body 20a, and molding of the shell layer 15 is performed by a continuous molding facility 30 to be described later, as a connected flexible tube assembly 21 in a state where a plurality of flexible tube assemblies 14 are connected integrally, via the joint member 20.

Figure 4:
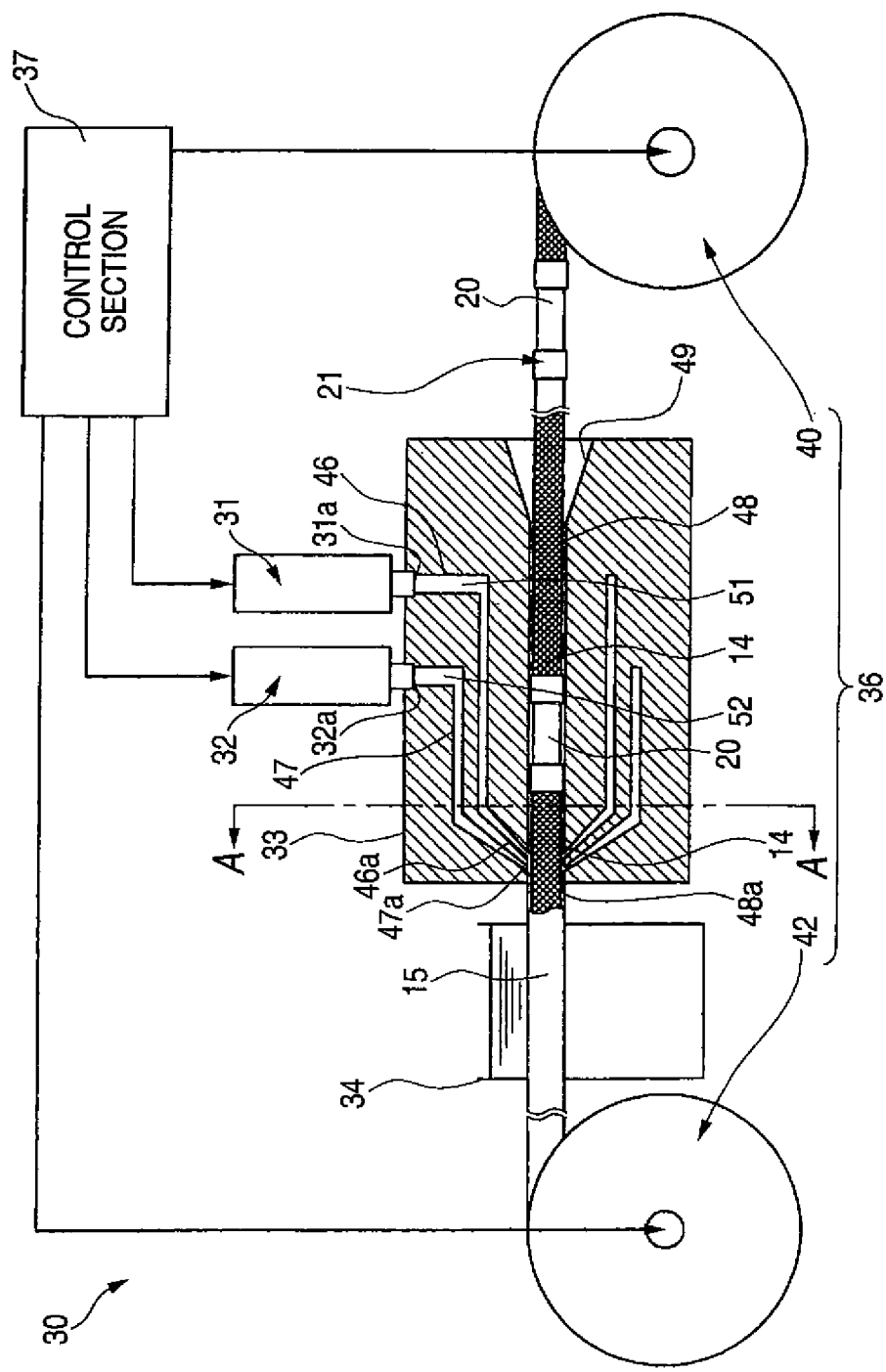
FIG. 4 is a block diagram showing a schematic configuration of a continuous molding facility in the respective embodiments.

The configuration of the continuous molding facility applied to this embodiment is shown in FIG. 4. The continuous molding facility 30 includes well-known extrusion sections 31 and 32 composed of screws, etc., a head section 33 for resin-molding the shell layer 15 on the outer peripheral surface of the connected flexible tube assembly 21, a cooling section 34, a conveyance section 36 which conveys the connected flexible tube assembly 21 to the head section 33, and a control section 37 which control them.

The conveyance section 36 is composed of a supply drum 40 and a winding drum 42, and the aforementioned connected flexible tube assembly 21 is wound around the supply drum 40, and is sequentially pulled out, and is wound around the winding drum 42 through the head section 33 in which the shell layer 15 is molded and the cooling section 34 by which the shell layer 15 after the molding is cooled. The rotation of the supply drum 40 and the rotation of the winding drum 42 are controlled by the control section 37, whereby the conveyance speed at which the connected flexible tube assembly 21 is conveyed is switched.

In the extrusion sections 31 and 32, discharge ports 31a and 32a are coupled with gates 46 and 47, respectively, of the head section 33, and extrude and supply molten soft and rigid resins 51 and 52 into the head section 33. In the extrusion sections 31 and 32 the extrusion amount (extrusion pressure) of resin is controlled by the control section 37. As the extrusion amount (extrusion pressure) of the extrusion sections 31 and 32 is controlled, the molding thicknesses of the rigid resin layer 18 and the soft resin layer 19 can be adjusted.

In this embodiment, when the molding shell layer 15 is molded, the control section 37 controls the extrusion amounts of the extrusion section 31 and 32 such that the ratio of the thicknesses of the rigid resin layer 18 and the soft resin layer 19 falls within a range of 1:9 to 9:1.

The head section 33 includes the gates 46 and 47 serving as passages for supplying the rigid resin 51 and the soft resin 52 in a molten state extruded from the aforementioned extrusion sections 31 and 32 to the connected flexible tube assembly 21. The head section 33 is formed with a circular hole 48 which determines the peripheral shape of the shell layer 15 molded at an outer periphery of the connected flexible tube assembly 21. Further, the head section 33 is provided with a conical recess 49 which is continuous with the circular hole 48 to guide insertion of the connected flexible tube assembly 21.

Figure 5:
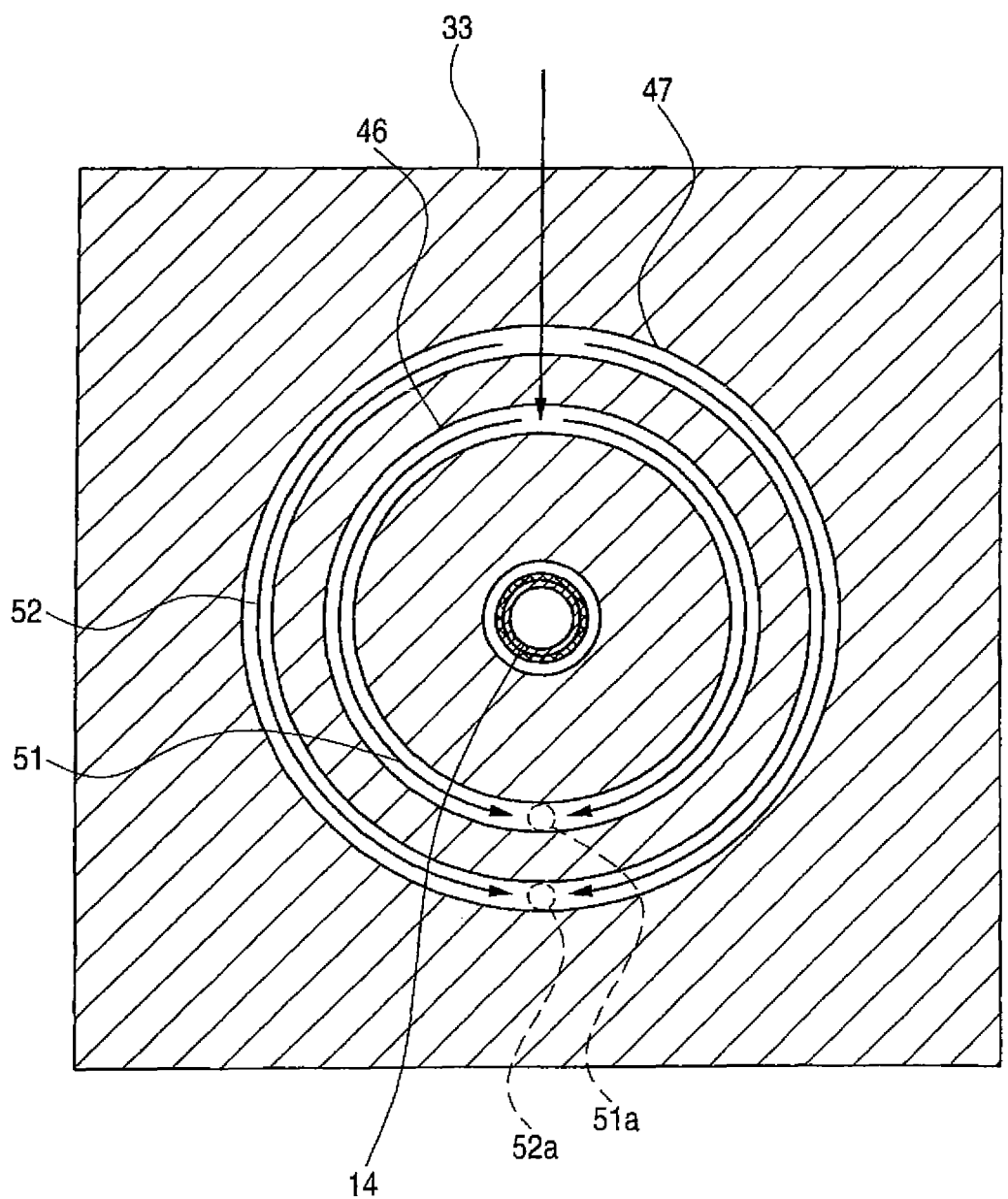
FIG. 5 is a sectional view of essential parts of a head section cut along a line A-A of FIG. 4.

As shown in FIG. 5, the gates 46 and 47 have a substantially cylindrical shape about the circular hole 48, and are formed such that their diameters become small gradually from the upstream toward the downstream, and supply ports 46a and 47a at the distal side thereof are continuous with the circular hole 48. In the gates 46 and 47, the rigid resin 51 and the soft resin 52 supplied from the extrusion sections 31 and 32, respectively, flow in from the above. Thus, welds 51a and 52a, i.e., portions in which resin stagnates are readily made lower positions of the gates 46 and 47 surrounded by dotted lines of FIG. 5.

The supply ports 46a and 47a of the gates 46 and 47 are in the vicinity of an outlet 48a of the circular hole 48, and the supply port 46a is located on the upstream side, and the supply 47a is located on the downstream side. Thereby, since the molten rigid resin 51 supplied from the gate 46 is laminated on the connected flexible tube assembly 21 earlier than the molten soft resin 52 supplied from the gate 47, the rigid resin layer 18 is formed in the lower layer, and the soft resin layer 19 is formed in the upper layer.

Moreover, the outlet 48a of the circular hole 48 in the head section 33 is formed such that its diameter matches the external diameter of the shell layer 15 formed at the outer periphery of the flexible tube assembly 14. As the connected flexible tube assembly 21 immediately after the rigid resin 51 and the soft resin 52 are laminated from the gates 46 and 47, respectively, passes through the outlet 48a, the flexible tube assembly is molded such that the external diameter of the shell layer 15 becomes uniform. The connected flexible tube assembly 21 of which the shell layer 15 is molded passes through the head section 33, and then passes through the cooling section 34. Cooling liquid, such as water, is stored in the cooling section 34, and as the flexible tube assembly passes through the inside of the cooling liquid, the shell layer 15 is cooled and cured. In addition, the invention is not limited thereto, and the cooling liquid, air, etc. may be blown against the shell layer 15 to cool it.

Figure 6:
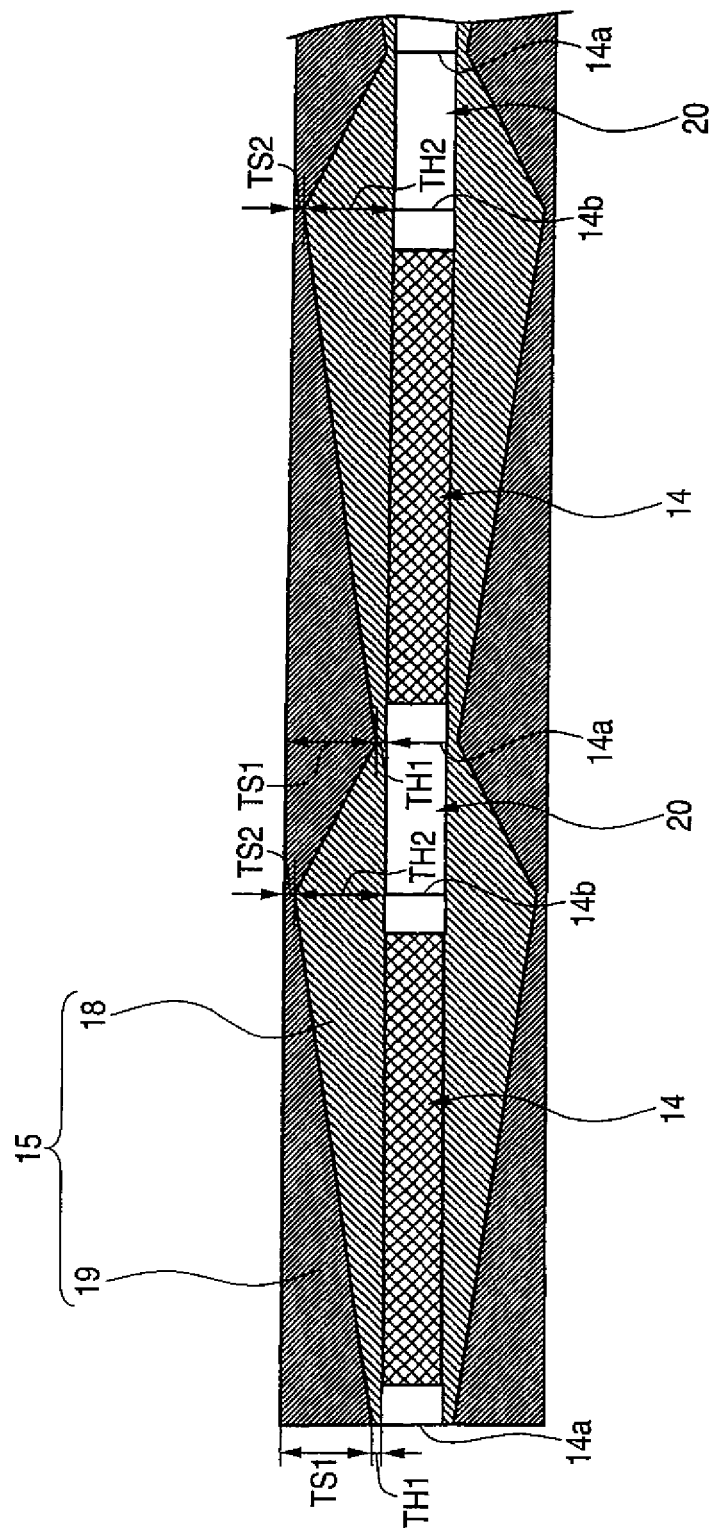
FIG. 6 is an explanatory view schematically showing the thickness variations of a rigid resin layer and a soft resin layer of a shell layer when a connected flexible tube assembly is molded, in the first embodiment.

The process when the shell layer 15 is molded on the connected flexible tube assembly 21 by the continuous molding facility 30 with the above configuration will be described with reference to FIG. 6. In addition, FIG. 6 schematically shows the thickness variations of the rigid resin layer 18 and the soft resin layer 19 when a molding step is performed, and shows the thickness of the shell layer 15 largely in order to make it grasped visually. Further, FIG. 6 shows a case where the shell layer 15 is molded to the right from the left in the drawing.

When the continuous molding facility 30 performs the molding step, the rigid resin 51 and the soft resin 52 in a molten state are extruded from the extrusion sections 31 and 32 to the head section 33, and the conveyance section 36 operates to convey the connected flexible tube assembly 21 to the head section 33. At this time, the extrusion sections 31 and 32 supply the resins to the head section 33 with a pump discharge amount shown in FIG. 6. Also, when the shell layer 15 is molded from the distal end 14a of the flexible tube assembly 14 to the proximal end 14b thereof, as shown in FIG. 6, the control section 37 controls the extrusion amounts of the resins by the extrusion sections 31 and 32 such that the ratio of the thickness TH1 of the rigid resin layer 18 and the thickness TS1 of the soft resin layer 19 is 1:9 at the distal end 14a of the flexible tube assembly 14, the ratio of the rigid resin layer 18 increases gradually toward the proximal end 14b of the flexible tube assembly 14 from the distal end 14a thereof whereby the ratio of the thicknesses is reversed, and the ratio of the thickness TH2 of the rigid resin layer 18 and the thickness TS2 of the soft resin layer 19 is 9:1 at the proximal end 14b of the flexible tube assembly 14.

On the other hand, when the shell layer is molded on the outer peripheral surface of the joint member 20, as shown in FIG. 6, the control section 37 controls the extrusion amounts of the extrusion sections 31 and 32 such that the ratio of the thickness TH2 of the rigid resin layer 18 and the thickness TS2 of the soft resin layer 19 is 9:1 in a position adjacent to the proximal end 14b of the flexible tube assembly 14, the ratio of the soft resin layer 19 increases gradually toward the distal end 14a of the flexible tube assembly 14 from the proximal end 14b of the flexible tube assembly 14, and the ratio of the thickness TH1 of the rigid resin layer 18 and the thickness TS1 of the soft resin layer 19 is 1:9 in a position adjacent to the distal end 14a of the next flexible tube assembly 14.

Further, when the shell layer 15 is molded from the distal end 14a of the flexible tube assembly 14 to the proximal end 14b thereof, similarly to the above, the extrusion sections 31 and 32 are controlled such that the ratio of the thickness TH1 of the rigid resin layer 18 and the thickness TS1 of the soft resin layer 19 is 1:9 at the distal end 14a; the thickness of the rigid resin layer 18 becomes large gradually toward the proximal end 14b, and the ratio of the thickness TH2 of the rigid resin layer 18 and the thickness TS2 of the soft resin layer 19 is 9:1 at the proximal end 14b. Thereafter, the shell layer 15 is molded on the connected flexible tube assembly 21 by performing switching the extrusion pressures of the extrusion sections 31 and 32 in a similar manner. Then, after the connected flexible tube assembly 21 in which the shell layer 15 is molded to the last end is detached from the continuous molding facility 30 and the coating film 16 is coated, the joint member 20 is detached whereby the molding step of the flexible tube 10 is completed.

By controlling the continuous molding facility 30 in this way, the shell layer can be molded without setting the thickness of the rigid resin layer or the soft resin layer to zero. Thus, it is not necessary to provide the head section 33 with bypass passages for discarding resin to the outside, and it is also not necessary to stop the discharge by the extrusion sections 31 and 32. Therefore, it becomes possible to manufacture the flexible tube 10 at low cost. Further, in a case where the discharge by the extrusion sections 31 and 32 is stopped, resin will remain in the positions of the aforementioned welds 51a and 52a. However, since molding can be performed in the continuous molding facility 30 in a state where rigid resin and soft resin are always extruded from the extrusion sections 31 and 32. Thus, in the circumferential direction of the flexible tube 10, the rigid resin layer 18 and the soft resin layer 19 hardly becomes nonuniform, so that uniform molding thicknesses can be obtained. Further, in the molding thickness of the flexible tube, the rigid resin layer 18 and the soft resin layer 19 have set molding thicknesses, so that molding of the shell layer can be performed precisely.

Although an example in which the ratio of the molding thicknesses of the rigid resin layer and the soft resin layer is 1:9 at the distal end of the flexible tube, and is 9:1 at the proximal end of the flexible tube is given in the first embodiment, the ratio of the thicknesses is not limited thereto, and any ratio may be adopted as long as the ratio of the molding thicknesses of the rigid resin layer and the soft resin layer falls within a range of 1:9 to 9:1.

Second and Third Embodiments

Figure 7:
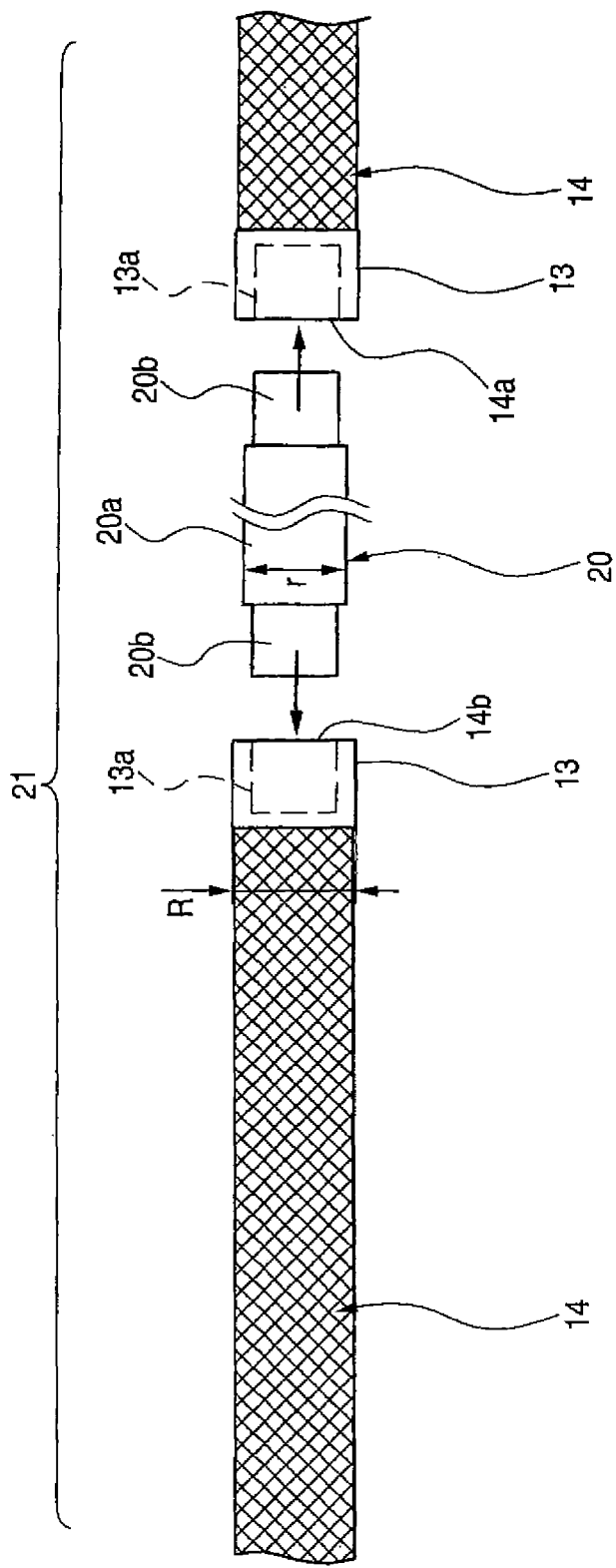
FIG. 7 is a plan view showing the configuration of a joint member which connects flexible tube assemblies together, in second and third embodiments.

In second and third embodiments, as shown in FIG. 7, the external diameter r of the main body 20a of the joint member 20 is smaller than the external diameter R of the flexible tube assembly 14. In addition, the invention is not limited thereto, and at least a portion of the joint member 20 has only to be smaller than the diameter of the flexible tube assembly 14. Further, the surface of the joint member 20 is coated with a separating material, such as Teflon (registered trademark), and thereby, the shell layer 15 molded on the outer peripheral surface of the joint member 20 is easily peeled off after the shell layer 15 is molded as the connected flexible tube assembly 21. In addition, when flexible tube assemblies 14 are connected together via the joint member 20, the connection is performed such that the distal ends 14a or proximal ends 14b of the flexible tube assemblies 14 face each other. Further, a main body 20a of the joint member 20 has flexibility. in order to return the thickness ratio of the resins to an initial value during molding of the shell layer 15 in the main body 20a, in the second embodiment, the main body is formed with a length about which the balance between the conveyance speed of continuous molding, and the variation of extrusion pressure of resin is taken into consideration, and in the third embodiment, the main body is formed with a length about which the balance between the conveyance speed of continuous molding, and the variation of the extrusion pressure of resin.

Figure 8:
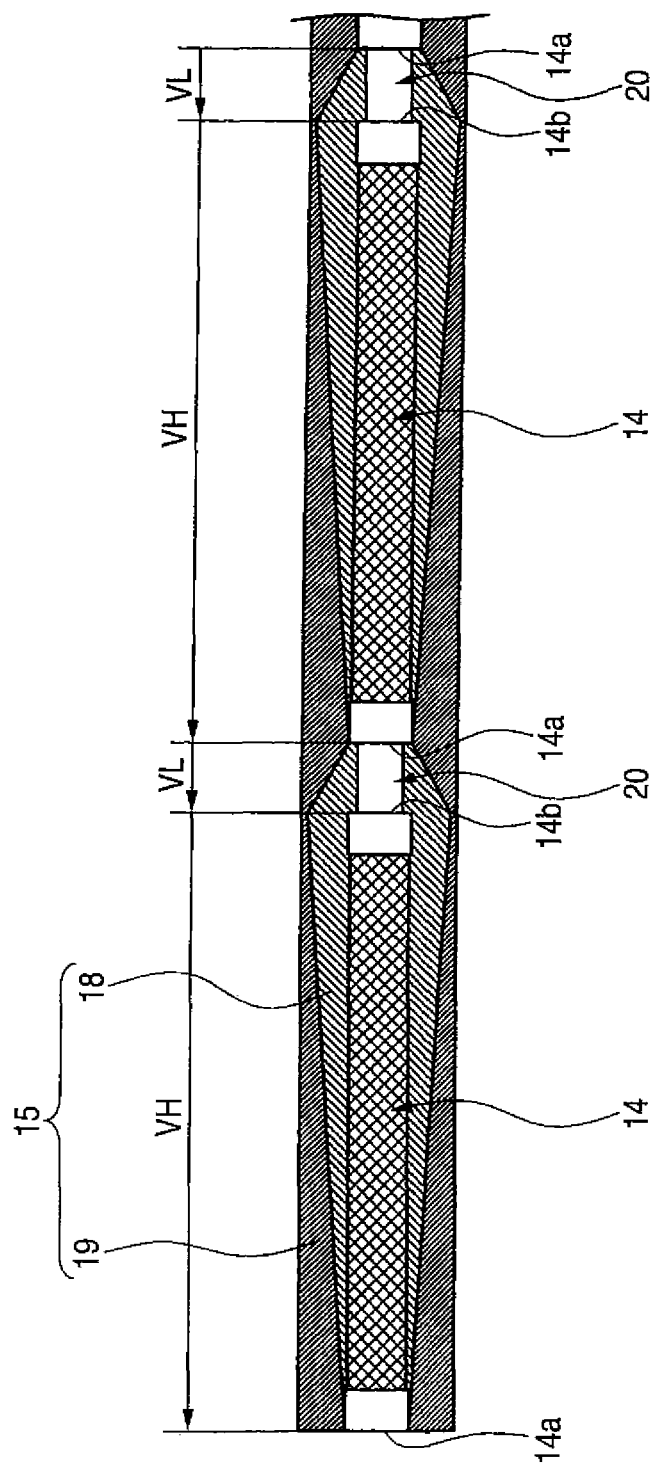
FIG. 8 is an explanatory view schematically showing the thickness variations of a rigid resin layer and a soft resin layer of a shell layer when a connected flexible tube assembly is molded, in the second embodiment.
Figure 9:
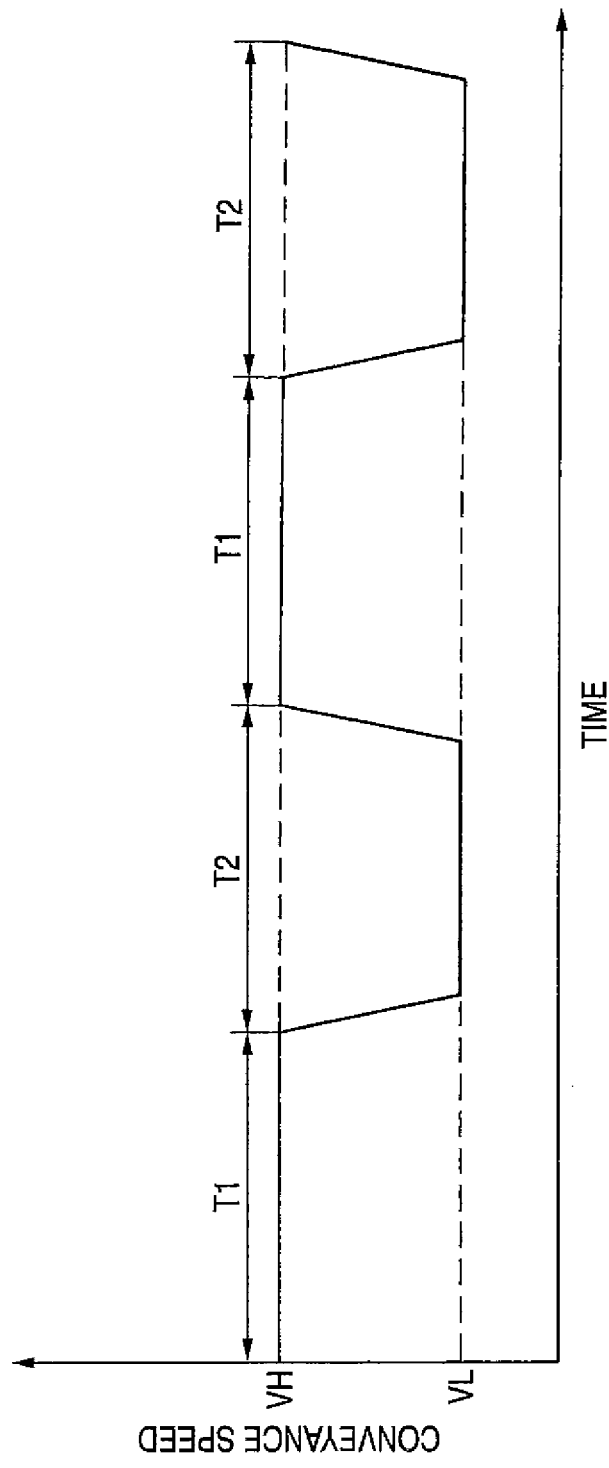
FIG. 9 is a graph showing the change of conveyance speed when the connected flexible tube assembly is molded, in the second embodiment.

The process when the shell layer 15 is molded on the connected flexible tube assembly 21 by the continuous molding facility 30 with the above configuration in the second embodiment will be described with reference to FIGS. 8 and 9. In addition, FIG. 8 schematically shows the thickness variations of the rigid resin layer 18 and the soft resin layer 19 when a molding step is performed, and shows the thickness of the shell layer 15 largely in order to make it grasped visually. Further, FIG. 8 shows a case where the shell layer 15 is molded to the right from the left in the drawing. FIG. 9 shows a conveyance speed change of the connected flexible tube assembly 21.

When the continuous molding facility 30 performs the molding step, the rigid resin 51 and the soft resin 52 in a molten state are extruded from the extrusion sections 31 and 32 to the head section 33, and the conveyance section 36 operates to convey the connected flexible tube assembly 21 to the head section 33. At this time, the extrusion sections 31 and 32 are in the state where they always extrude the rigid resin 51 and the soft resin 52 to supply them to the head section 33. Also, when the shell layer 15 is molded from the distal end 14a of the flexible tube assembly 14 to the proximal end 14b thereof, as shown in FIG. 8, the control section 37 controls the extrusion pressures of the resins by the extrusion sections 31 and 32 such that the thickness of the soft resin layer 19 is larger than that of the rigid resin layer 18 at the distal end 14a of the flexible tube assembly 14, the ratio of the rigid resin layer 18 increases gradually toward the proximal end 14b of the flexible tube assembly 14 from the distal end 14a thereof, and the thickness of the rigid resin layer 18 becomes larger than that of the soft resin layer 19 at the proximal end 14b of the flexible tube assembly 14. Moreover, the control section 37 controls the conveyance section 36 so as to convey the connected flexible tube assembly 21 at a predetermined conveyance speed VH when molding from the distal end 14a of the flexible tube assembly 14 to the proximal end 14b thereof is performed, that is, in a time period shown by reference numeral T1 of FIG. 9.

On the other hand, when the shell layer is molded on the outer peripheral surface of the joint member 20, as shown in FIG. 8, the control section 37 controls the extrusion amounts of the extrusion sections 31 and 32 such that the thickness of the rigid resin layer 18 becomes larger than that of the soft resin layer 19 in a position adjacent to the proximal end 14b of the flexible tube assembly 14, the ratio of the soft resin layer 19 increases gradually toward the distal end 14b from the proximal end 14a of the flexible tube assembly 14, and the thickness of the soft resin layer 19 becomes larger than that of the rigid resin layer 18 at the distal end 14b of the next flexible tube assembly 14. Moreover, the control section 37 controls the conveyance section 36 so as to convey the connected flexible tube assembly 21 at a conveyance speed VL which is slower than the conveyance speed VH, when the shell layer 15 is molded on the outer peripheral surface of the joint member 20, that is, in a time period shown by reference numeral T2 of FIG. 9. By changing the conveyance speed in this way, the time period T1 during which the flexible tube assembly 14 with long total length is molded and the time period T2 during which the flexible tube assembly 14 with short total length is molded are approximately equal to each other. In addition, the timing with which this conveyance speed is switched is matched with, for example, when the proximal end 14b of the flexible tube assembly 14 passes through the outlet 48a of the head section 33.

Also, when the shell layer 15 is molded from the distal end 14a of the flexible tube assembly 14 to the proximal end 14b thereof, similarly, the extrusion sections 31 and 32 are controlled such that the thickness of the rigid resin layer 18 becomes large gradually toward the proximal end 14b from the distal end 14a, and the conveyance section 36 is controlled such that the conveyance speed is switched whereby the connected flexible tube assembly 21 is conveyed at the conveyance speed VH. Thereafter, the shell layer 15 is molded on the connected flexible tube assembly 21 by performing switching the extrusion pressures of the extrusion sections 31 and 32 and switching of the conveyance speed by the conveyance section 36 in a similar manner. Then, after the connected flexible tube assembly 21 in which the shell layer 15 is molded to the last end is detached from the continuous molding facility 30 and the coating film 16 is coated, the joint member 20 is detached whereby the molding step of the flexible tube 10 is completed. In addition, when the joint member 20 is detached, the separating material is coated as described above. Therefore, it is possible to easily peel off the shell layer 15 from the joint member 20, the joint member 20 from which the shell layer 15 is peeled is cleaned, and is repeatedly used for connection of the flexible tube assembly 14.

By controlling the continuous molding facility 30 in this way, the conveyance time when the outer periphery of the joint member 20 is molded can be lengthened. Therefore, the extrusion pressures of the extrusion sections 31 and 32 when the shell layer 15 is molded on the outer periphery of the flexible tube assembly 14 are sufficiently allowed to return to initial extrusion pressures to the position of the distal end 14a of the next flexible tube assembly 14. Consequently, even if the total length of the joint member 20 is shortened, it is possible to continuously and reliably perform molding of the shell layer 15 while the soft resin layer 19 and the rigid resin layer 18 are laminated in a predetermined ratio, and it is possible to manufacture more flexible tube 10 in one molding step as the joint member 20 is made shorter. Thus, the manufacturing efficiency can be improved, and the cost can be reduced. In addition, when the shell layer 15 of the joint member 20 is molded, there is a probability that the resin layers are formed more thickly as the conveyance speed becomes slower. However, by making the diameter r of the joint member 20 smaller than the diameter R of the flexible tube assembly 14 as the thickness increases, thereby correcting the external diameter, it is possible to mold the shell layer 15 with a uniform external diameter.

Figure 10:
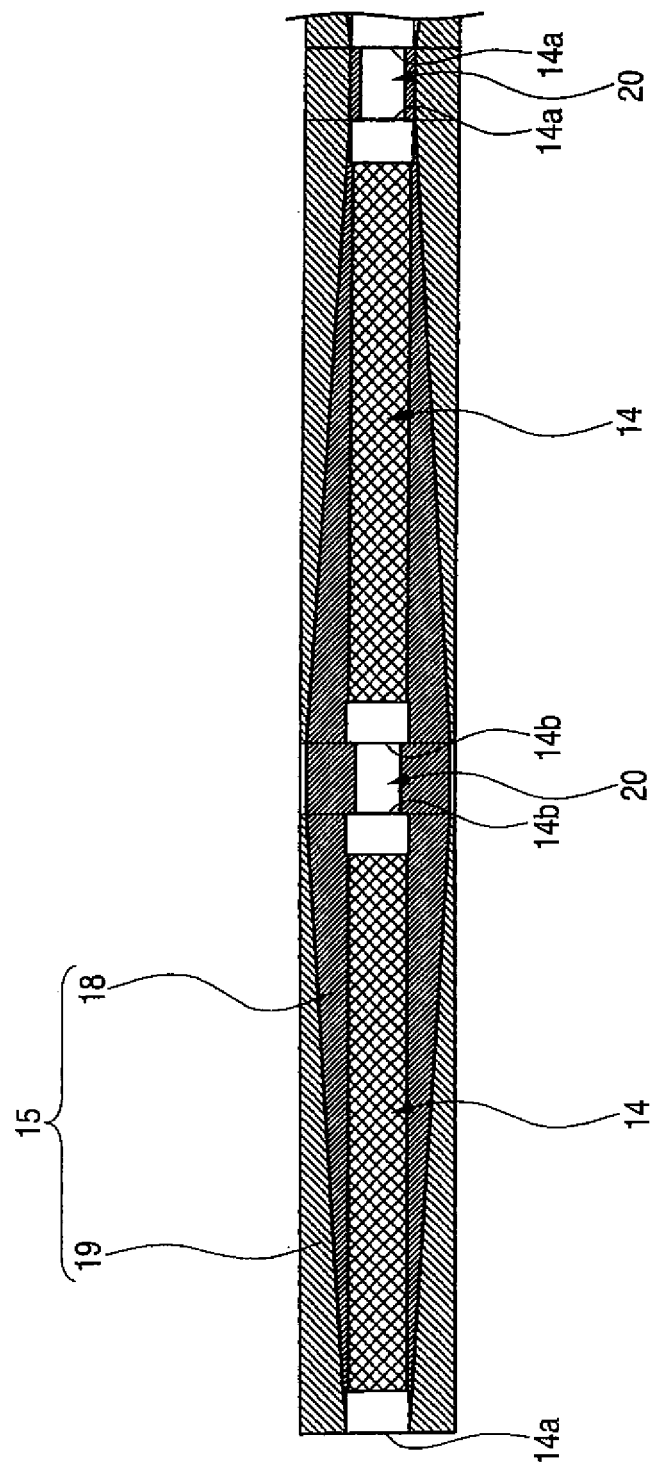
FIG. 10 is an explanatory view schematically showing the thickness variations of a rigid resin layer and a soft resin layer of a shell layer when a connected flexible tube assembly is molded, in the third embodiment.

The process when the shell layer 15 is molded on the connected flexible tube assembly 21 by the continuous molding facility 30 with the above configuration in the third embodiment will be described with reference to FIG. 10. In addition, FIG. 10 schematically shows the thickness variations of the rigid resin layer 18 and the soft resin layer 19 when a molding step is performed, and shows the thickness of the shell layer 15 largely in order to make it grasped visually. Further, FIG. 10 shows a case where the shell layer 15 is molded to the right from the left in the drawing.

When the continuous molding facility 30 performs the molding step, the rigid resin 51 and the soft resin 52 in a molten state are extruded from the extrusion sections 31 and 32 to the head section 33, and the conveyance section 36 operates to convey the connected flexible tube assembly 21 to the head section 33. At this time, the extrusion sections 31 and 32 are in the state where they always extrude the rigid resin 51 and the soft resin 52 to supply them to the head section 33. First, when the shell layer 15 is molded from the distal end 14a of the flexible tube assembly 14 to the proximal end 14b thereof, as shown in FIG. 10, the control section 37 controls the extrusion pressures of the resins by the extrusion sections 31 and 32 such that the thickness of the soft resin layer 19 is larger than that of the rigid resin layer 18 at the distal end 14a of the flexible tube assembly 14, the ratio of the rigid resin layer 18 increases gradually toward the proximal end 14b of the flexible tube assembly 14 from the distal end 14a thereof, and the thickness of the rigid resin layer 18 becomes larger than that of the soft resin layer 19 at the proximal end 14b of the flexible tube assembly 14.

Subsequently, when the shell layer is molded on the outer peripheral surface of the joint member 20, the extrusion pressures of the resins by the extrusion sections 31 and 32 are kept constant such that the ratios of the rigid resin layer 18 and the soft resin layer 19 are equal to each other from a position adjacent to the proximal end 14b of the flexible tube assembly 14 to a position adjacent to the proximal end 14b of the next flexible tube assembly 14, that is, the thickness of the rigid resin layer 18 is larger than the soft resin layer 19.

Then, when the shell layer 15 is molded from the proximal end 14b of the next flexible tube assembly 14 to the distal end 14a thereof, the molding is performed such that the ratio of the soft resin and the rigid resin may return to an initial value. That is, the control section 37 controls the extrusion pressures of the resins by the extrusion sections 31 and 32 such that the ratio the rigid resin layer 18 decreases gradually toward the distal end 14a of the flexible tube assembly 14 from the proximal end 14b thereof, and the thickness of the soft resin layer 19 becomes larger than the rigid resin layer 18 at the distal end 14a of the flexible tube assembly 14, contrary to the previous procedure.

When the shell layer 15 is molded on the outer peripheral surface of the next joint member 20, the extrusion pressures of the resins by the extrusion sections 31 and 32 are kept constant such that the ratios of the rigid resin layer 18 and the soft resin layer 19 are equal to each other from a position adjacent to the distal end 14a of the flexible tube assembly 14 to a position adjacent to the distal end 14a of the next flexible tube assembly 14, that is, the thickness of the soft resin layer 19 is larger than the rigid resin layer 18. The following procedure is the same as the procedure of the second embodiment.

By controlling the continuous molding facility 30 in this way, the extrusion pressures of the extrusion sections 31 and 32 when the shell layer 15 is molded on the outer periphery of the flexible tube assembly 14 are reversed when the outer periphery of the next flexible tube assembly 14 is molded, and is allowed to return to initial extrusion pressures to the position of the distal end 14a of the next flexible tube assembly 14. Consequently, even if the total length of the joint member 20 is shortened, it is possible to continuously and reliably perform molding of the shell layer 15 while the soft resin layer 19 and the rigid resin layer 18 are laminated in a predetermined ratio, and it is possible to manufacture more flexible tube 10 in one molding step as the joint member 20 is made shorter. Thus, the manufacturing efficiency can be improved, and the cost can be reduced.

Fourth Embodiment

Figure 11:
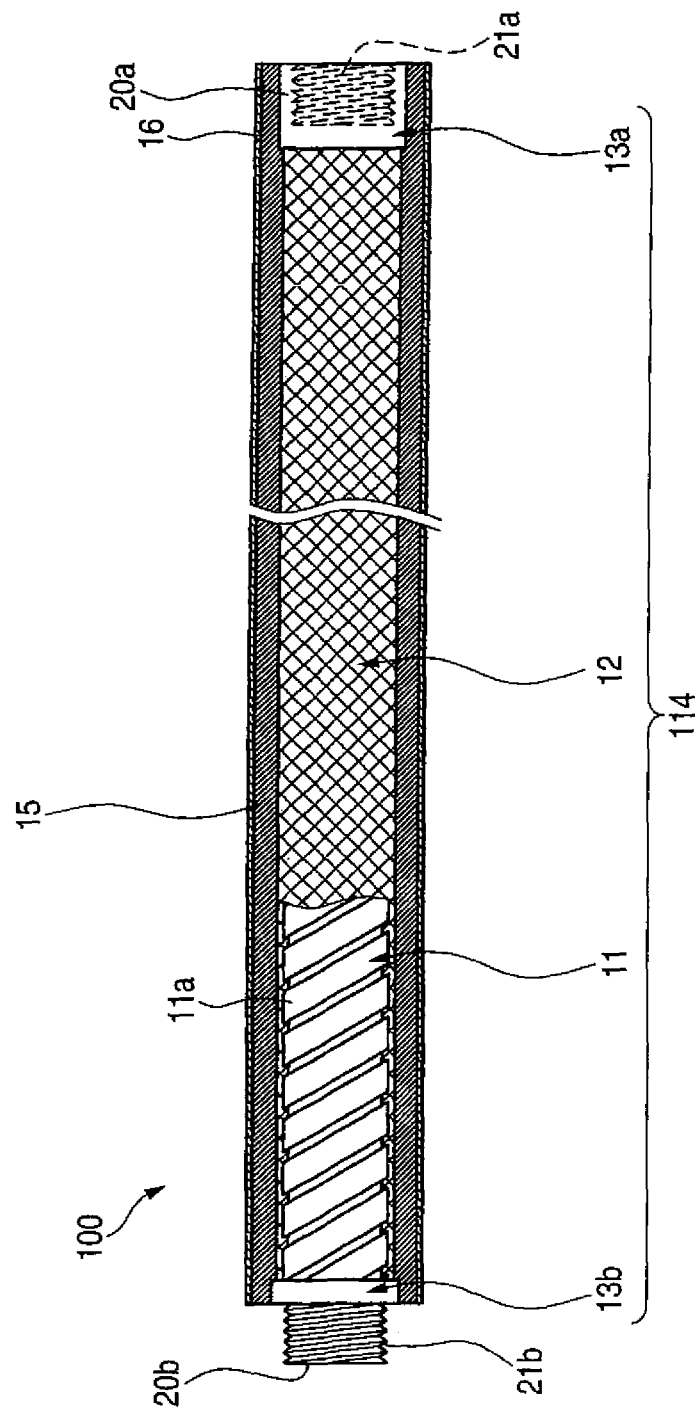
FIG. 11 is an enlarged fragmentary sectional view showing the configuration of an endoscope flexible tube in a fourth embodiment.
Figure 12:
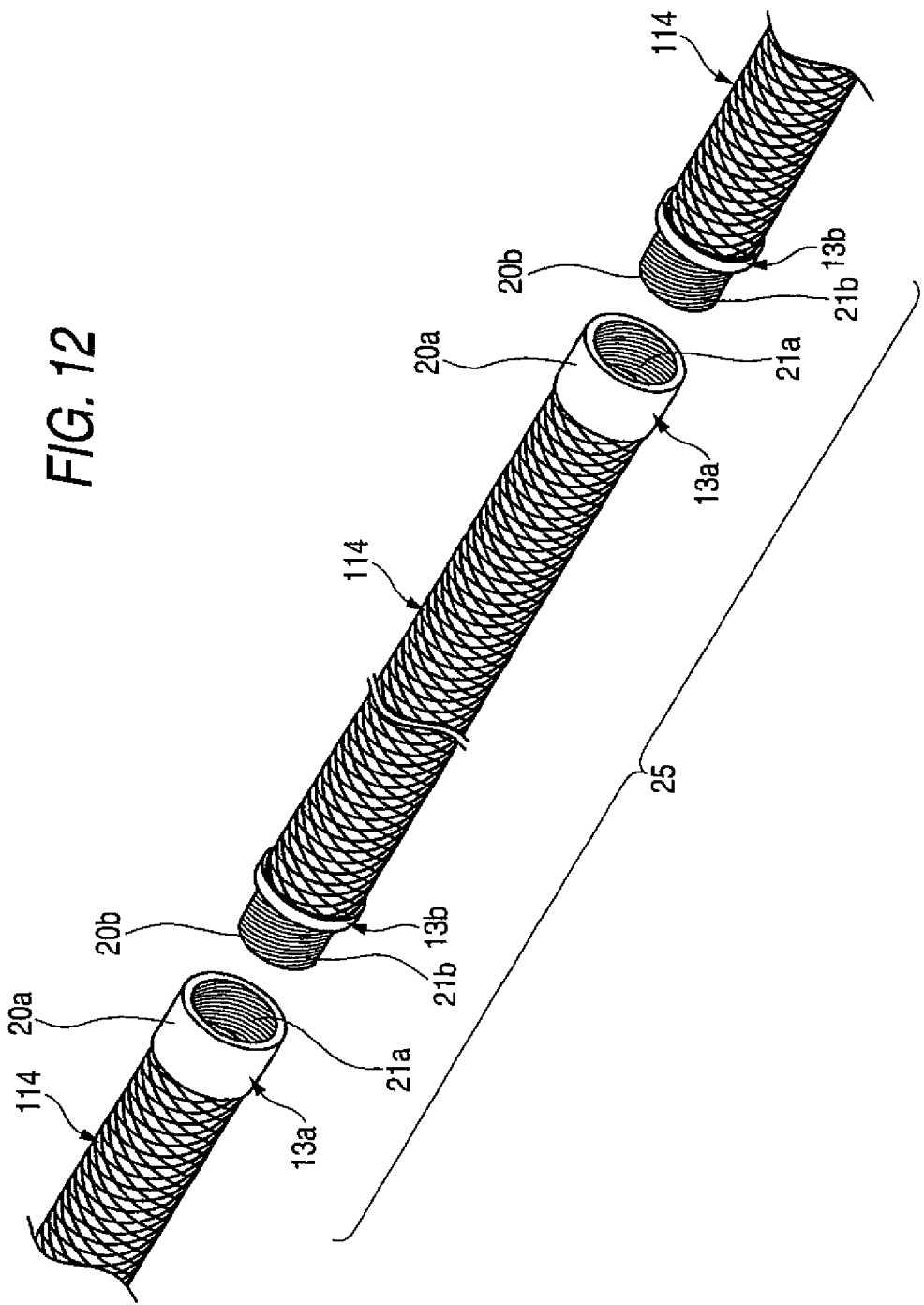
FIG. 12 is a plan view showing the configuration of a joint member which connects flexible tube assemblies together in the fourth embodiment.

Although the basic configuration of the flexible tube portion 3a is the same as that of the first to third embodiments, specifically, a flexible tube 100 which constitutes the flexible tube portion 3a in the fourth embodiment, as shown in FIG. 11, is configured such that a flexible tube assembly 114 is obtained by covering a helical tube 11 formed by spirally winding a metallic strip 11a on the innermost side with a tubular net body 12 made by weaving a metallic wire, and fitting mouthpieces 13a and 13b into both ends thereof, and a shell layer 15 made of urethane resin, etc. is laminated on an outer peripheral surface of the assembly. In addition, a mouthpiece attached to the distal side of the flexible tube assembly 114 and a mouthpiece attached to the proximal side thereof will be described below using reference numerals 13a and 13b, respectively. In this case, the distal side is an end on the side where the aforementioned angle portion 3b is connected, and the proximal end 14b is an end on the side where the body operation portion 5 is connected.

Coupling portions 20a and 20b are integrally provided in the mouthpieces 13a and 13b, respectively, and the coupling portions 20a and 20b are used to connect the flexible tube assemblies 114 together. The first coupling portion 20a has a substantially cylindrical shape which is continuous with the mouthpiece 13a, and has a female thread portion 21a formed at the inner peripheral surface thereof. The second coupling portion 20b has a substantially cylindrical shape whose external diameter is slightly smaller than the mouthpiece 13b over its entire periphery, and has a male thread portion 21b screwed to the female thread portion 21a formed at the outer peripheral surface thereof. Also, a connected flexible tube assembly 25 in a state where a plurality of flexible tube assemblies 114 are integrally connected by screwing the male thread portion 21b of a flexible tube assembly 114 to the female thread portion 21a of another flexible tube assembly 114 is obtained. In the state where the connected flexible tube assembly 25 is obtained, the molding of the shell layer 15 by the continuous molding facility 30 to be described later is performed.

In addition, in a case where the flexible tube 100 with the above configuration is applied to the flexible tube portion 3a of an endoscope, when the angle portion 3b is connected to the mouthpiece 13a at the distal side by soldering, the soldering can be easily performed, for example, by making the end of the angle portion 3b abut on the inner peripheral surface of the female thread portion 21a, and making solder flow into and stay in grooves of the female thread portion 21a. Further, even when the body operation portion 5 is connected to the mouthpiece 13b at the proximal side, similarly, the soldering may be performed by making solder stagnate in grooves of the male thread portion 21b, or the connection may be performed by providing a female thread portion in the body operation portion 5, and screwing the male thread portion 21b to the female thread portion.

As described above, when a plurality of flexible tube assemblies 114 are connected together, it is possible to easily and reliably connect the assemblies by screwing the female thread portion 21a of a flexible tube assembly 114 and the male thread portion 21b of another flexible tube assembly together, and a plurality of flexible tube assemblies 14 can be continuously made into the connected flexible tube assembly 25 without using any jig unlike a conventional manufacturing method. As a method of providing the shell layer 15 in the connected flexible tube assembly 25, a well-known molding method of utilizing a well-known molding facility can be mentioned. However, the continuation molding method using the continuous molding facility 30, which have been described in the above first to third embodiments, can be mentioned preferably. When the shell layer 15 is molded in the connected flexible tube assembly 25 by the continuous molding facility 30, the assemblies are reliably coupled together by screwing of the male thread portion 21b and the female thread portion 21a. Thus, the molding step can be smoothly performed without disconnection of the flexible tube assemblies 14.

Although the configuration in which flexible tube assemblies are coupled together by screwing of the female thread portion 21a and the male thread portion 21b is illustrated in the above embodiments, the invention is not limited thereto, the flexible tube assemblies may be coupled together as a structure as shown in FIG. 13. In the flexible tube assembly 50 shown in FIG. 13, coupling portions 51a and 51b are integrally provided in the mouthpieces 13a and 13b, respectively. Flexible tube assemblies 114 are connected together using these coupling portions. In the first coupling portion 51a, in a cylindrical portion 54 which is continuous with the mouthpiece 13a, longitudinal slits 54a are formed along the axial direction from an end surface of the cylindrical portion 54, and lateral slits 54b which are cut away in the peripheral direction continuously with the longitudinal slits 54a, respectively, are formed. The second coupling portion 51b is smaller in external diameter than the mouthpiece 13b over its entire periphery, and its outer peripheral surface is composed of a cylindrical portion 55 on which the inner peripheral surface of the cylindrical portion 54 fits, and convex portions 56 which protrude from the circumferential surface of the cylindrical portion 55. In addition, the longitudinal slits 54a and the lateral slits 54b are formed with almost the same width as the convex portions 56.

Figure 14A:
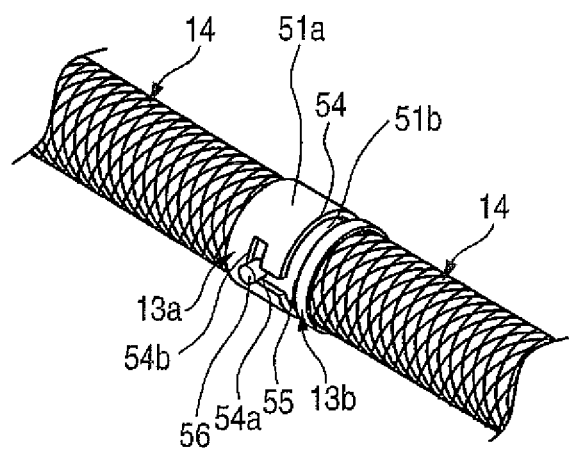
FIGS. 14A and 14B are explanatory views showing a state when the coupling portions shown in FIG. 13 are connected together.
Figure 14B:
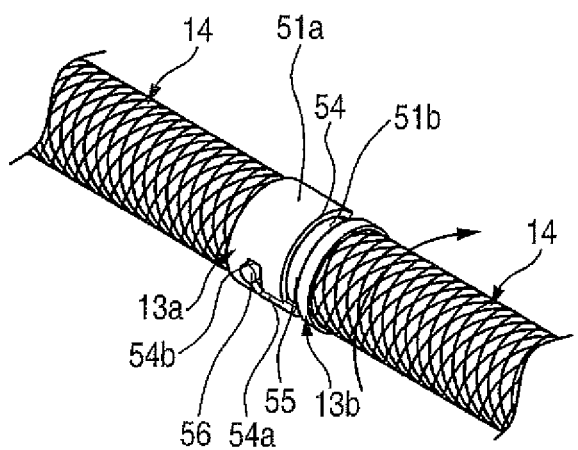

Also, when the coupling portion 51a of a flexible tube assembly 114 is copied with the coupling portion 51b of another flexible tube assembly 114, the convex portions are pushed into the longitudinal slits 54a until the convex portions bump against the inner portions of the longitudinal slits by making the outer peripheral surface of the cylindrical portion 55 fit to the inner peripheral surface of the cylindrical portion 54 while the convex portions 56 are inserted into the longitudinal slits 54a, respectively (state shown in FIG. 14A). Thereafter, if the second coupling portion 51b is rotated clockwise relative to the first coupling portion 51a, the convex portions 54 are engaged with the lateral slits 56b, respectively. Thereby, the coupling can be performed so that the first coupling portion may not be detached from the second coupling portion 51b (state shown in FIG. 14B). By coupling the first and second coupling portions 51a and 51b together, a connected flexible tube assembly 60 in a state where a plurality of flexible tube assemblies 50 are connected together is obtained. By adopting such a configuration, it is possible to simply and reliably connect the flexible tube assemblies 50 together. Also, since the coupling is not released in the molding step, the same effects as the above embodiments can be obtained.

In addition, in the above first to third embodiments, when a shell layer is molded, the shell layer is molded as a two-layer structure in which a rigid resin is molded in a lower layer, and a soft resin is molded in an upper layer, and the thicknesses of these resin layers are changed to give changes to the pliability of a flexible tube such that high pliability is given to one end of the flexible tube, and the pliability becomes lower at the other end of the flexible tube. However, the invention is not limited thereof. For example, as described in JP-A-2-131738, a soft resin and a rigid resin may be mixed together to mold a shell layer, and the mixing ration thereof may be changed to give changes to the pliability of a flexible tube.

Further, in each of the above embodiments, the electronic endoscope which observes an image which is obtained by photographing the state of a subject to be inspected using an imaging device is described as an example. However, the invention is limited thereto, and can also be applied to an endoscope which adopts an optical image guide to observe the state of a subject to be inspected. Further, although the flexible tube which constitutes the insertion portion 3 is illustrated in the above-mentioned embodiments, the invention is not limited thereto. For example, the invention can also be applied to a universal cord composed of components equivalent to the flexible tube which constitutes the insertion portion 3. In this case, the thickness of a rigid resin at one side of the side where the universal cord is connected to a processor, etc. and the side where the universal cord is connected to the body operation portion 5 can be made large, and the thickness of a soft resin at the other side can be made large.

According to the endoscope flexible tube of the invention, the shell layer has the two-layer structure of a rigid resin layer made of a rigid resin, and a soft resin layer made of a soft resin, and the two-layer structure is maintained over the entire flexible tube in its length direction (particularly, the thickness ratio of the soft resin layer and the rigid resin layer falls within a range of 1:9 to 9:1). Thereby, it is possible to obtain an endoscope flexible tube in which the soft resin layer and the rigid resin layer of the flexible tube are molded such that their thicknesses in the peripheral direction are uniform, and their molding thicknesses in the axial direction are adjusted precisely.

According to the manufacturing method of an endoscope flexible tube of the invention, the endoscope flexible tube of the invention is manufactured by continuously molding a shell layer including a rigid resin and a soft resin on outer surfaces of a plurality of tubular structures having flexibility while the tubular structures are conveyed in a connected state. Thus, the outer layers of flexible tubes can be molded efficiently, and can be manufactured at low cost.

If the first coupling portion and the second coupling portion are provided in advance at one end of the tubular structure and at the other end thereof, respectively, the first coupling portion, and the second coupling portion provided in a separate tubular structure are coupled together to connect the cylindrical structures, it is possible to mold a plurality of flexible tubes at a time without using connecting members, such as C-shaped clips, and manufacture them at lower cost. Further, particularly, when the shell layer is molded at an outer periphery of the tubular structure, the shell layer is molded such that the ratio of the rigid resin increases gradually toward the other end from the one end at one end of the tubular structure, and the ratio of the soft resin is larger than the rigid resin at the other end of the tubular structure; when the shell layer is molded on the outer periphery of the connecting member, the shell layer is molded such that the ratio of the soft resin layer increases gradually from the other end of the tubular structure toward the one end of the next tubular structure, and the ratio of the soft resin layer becomes larger than that of the rigid resin layer in a position adjacent to the one end of the next tubular structure; and the conveyance speed when the shell layer is molded at the outer periphery of the connecting member is made slower than that when the shell layer is molded at the outer periphery of the tubular structure. If so, the connecting member can be shortened to increase the number of flexible tubes which can be molded at a time. Thus, the outer layers of flexible tubes can be molded efficiently, and can be manufactured at low cost.

Further, particularly, when the shell layer is molded at the outer periphery of the tubular structure, the shell layer is molded such that the ratio of the soft resin and the rigid resin changes gradually from the one end of the tubular structure toward the other end thereof, and then, when the shell layer is molded at the outer periphery of the next tubular structure, the shell layer is molded such that the ratio of the soft resin and the rigid resin returns to an initial value from the one end of the tubular structure toward the other end thereof. If so, the connecting member can be shortened to increase the number of flexible tubes which can be molded at a time. Thus, the outer layers of flexible tubes can be molded efficiently, and can be manufactured at low cost.

The entire disclosure of each and every foreign patent application from which the benefit of foreign priority has been claimed in the present application is incorporated herein by reference, as if fully set forth.

What is claimed is:

1. A manufacturing method of an endoscope flexible tube comprising a tubular structure having flexibility; and a shell layer on an outer peripheral surface of the tubular structure, the method comprising:
   continuously molding the shell layer including a rigid resin and a soft resin on outer surfaces of a plurality of tubular structures having flexibility and outer surfaces of connecting members while the tubular structures are connected by the connecting members and conveyed in a connected state;
   wherein the shell layer has a two-layer structure including a rigid resin layer of the rigid resin and a soft resin layer of the soft resin,
   wherein the two-layer structure is maintained over the entire flexible tube in its length direction,
   wherein a thickness ratio of the soft resin layer and the rigid resin layer falls within a range of 1:9 to 9:1,
   wherein each of said plurality of tubular structures having flexibility comprises a first coupling portion at its rear end and a second coupling portion at its distal end,
   wherein said plurality of tubular structures are connected while the first coupling portion of one of the tubular structures is connected to the second coupling portion of next one of the tubular structures via one of the connecting members,
   wherein the thickness ratio of the soft resin layer and the rigid resin layer covering the one of the connecting members at a portion adjacent to the first coupling portion of the one of the tubular structures corresponds to the thickness ratio of the soft resin layer and the rigid resin layer covering the one of the tubular structures at the first coupling portion of the one of the tubular structures, and
   wherein the thickness ratio of the soft resin layer and the rigid resin layer covering the one of the connecting members at a portion adjacent to the second coupling portion of the next one of the tubular structures corresponds to the thickness ratio of the soft resin layer and the rigid resin layer covering the next one of the tubular structures at the second coupling portion of the next one of the tubular structures.

2. The manufacturing method of an endoscope flexible tube according to claim 1,
   wherein when the shell layer is molded at an outer periphery of the tubular structures, the shell layer is molded such that a ratio of the soft resin is larger than that of the rigid resin at one end of one of the tubular structures, a ratio of the rigid resin increases gradually toward the other end from the one end of the one of the tubular structures, and the ratio of the rigid resin is larger than that of the soft resin at the other end;
   when the shell layer is molded on an outer periphery of the connecting member, the shell layer is molded such that the ratio of the rigid resin becomes larger than that of the soft resin in a position adjacent to the other end of the one of the tubular structures, the ratio of the soft resin increases gradually from the other end of the one of the tubular structures toward one end of next one of the tubular structures, and the ratio of the soft resin becomes larger than that of the rigid resin in a position adjacent to the one end of the next one of the tubular structures; and
   a conveyance speed of said plurality of tubular structures when the shell layer is molded at the outer periphery of the connecting member is made slower than that when the shell layer is molded at the outer periphery of the tubular structure.

3. The manufacturing method of an endoscope flexible tube according to claim 1,
   wherein when the shell layer is molded, the shell layer is molded as a two-layer structure in which the rigid resin is formed in a lower layer and the soft resin is formed in an upper layer.

4. The manufacturing method of an endoscope flexible tube according to claim 1,
   wherein at least a portion of the connecting member has a diameter smaller than that of the tubular structures.

5. The manufacturing method of an endoscope flexible tube according to claim 1,
   wherein when the shell layer is molded at an outer periphery of the tubular structures, the shell layer is molded such that a ratio of the soft resin and the rigid resin changes gradually from one end of one of the tubular structures toward the other end of the one of the tubular structures, and then, when the shell layer is molded at an outer periphery of next one of the tubular structure, the shell layer is molded such that the ratio of the soft resin and the rigid resin returns to an initial value at the one end of the one of the tubular structures from one end of the next one of the tubular structures toward the other end of the next one of the tubular structures.

6. The manufacturing method of an endoscope flexible tube according to claim 5,
   wherein when the shell layer is molded, the shell layer is molded as a two-layer structure in which the rigid resin is formed in a lower layer, and the soft resin is formed in an upper layer.

\* \* \* \* \*